United States Patent
Gornik et al.

(10) Patent No.: US 11,454,636 B2
(45) Date of Patent: Sep. 27, 2022

(54) PROCEDURE OF PREDICTING TYPE 2 DIABETES DEVELOPMENT THROUGH ANALYSIS OF N-GLYCANS ATTACHED TO THE PLASMA PROTEINS OF A HEALTHY PERSON

(71) Applicant: GENOS d.o.o., Osijek (HR)

(72) Inventors: Olga Gornik, Zagreb (HR); Gordan Lauc, Zagreb (HR); Frano Vuckovic, Zagreb (HR); Ivan Gornik, Zagreb (HR)

(73) Assignee: GENOS d.o.o., Osijek (HR)

( * ) Notice: Subject to any disclaimer, the term of this patent is extended or adjusted under 35 U.S.C. 154(b) by 948 days.

(21) Appl. No.: 16/307,271

(22) PCT Filed: Jun. 5, 2017

(86) PCT No.: PCT/EP2017/063619
§ 371 (c)(1),
(2) Date: Dec. 5, 2018

(87) PCT Pub. No.: WO2017/215973
PCT Pub. Date: Dec. 21, 2017

(65) Prior Publication Data
US 2019/0195890 A1 Jun. 27, 2019

(30) Foreign Application Priority Data

Jun. 13, 2016 (HR) .................. P20160662A (51) Int. Cl.
*G01N 5/00* (2006.01)
*G01N 33/68* (2006.01)
(Continued)

(52) U.S. Cl.
CPC ......... *G01N 33/6893* (2013.01); *G01N 30/72* (2013.01); *G01N 2030/027* (2013.01);
(Continued)

(58) Field of Classification Search
CPC ......... G01N 33/57415; G01N 33/6848; G01N 2333/912; G01N 2560/00;
(Continued)

(56) References Cited

U.S. PATENT DOCUMENTS

| | | |
|---|---|---|
| 2007/0059722 A1 | 3/2007 | Salonen et al. |
| 2014/0120559 A1 | 5/2014 | Schaefer |
| 2015/0193587 A1 | 7/2015 | Urdea et al. |

FOREIGN PATENT DOCUMENTS

| | | | |
|---|---|---|---|
| WO | 2010029170 A2 | 3/2010 | |
| WO | 2014203010 A1 | 12/2014 | |
| WO | WO-2014203010 A1 * | 12/2014 | ............. G01N 30/72 |

OTHER PUBLICATIONS

Akmacic et al., High-Throughout Glycomics: Optimization of Sample Preparation, Biochemistry (Moscow), 2015, vol. 80, No. 7, pp. 934-942.
Friedman et al., Regularization Paths for Generalized Linear Models via Coordinate Descent, Journal of Statistical Software, Jan. 2010, vol. 33, Issue 1, 22 pages.
(Continued)

*Primary Examiner* — Michael Maskell
(74) *Attorney, Agent, or Firm* — RatnerPrestia (57) ABSTRACT

A prediction of type 2 diabetes development through quantitative analysis of N-glycans attached to the plasma proteins of a healthy person, which enables determination of whether the investigated person belongs to a risk group for type 2 diabetes development in the future. Using obtained quantitative percentages of all analyzed N-glycans as input variables of a model F: F(GP1, GP2, . . . , GPX; D, S), where X, D and S are parameters of the model F: X=total number of analyzed N-glycans; D=age of the investigated person; S=sex of the investigated person; male=1, female=0. Obtaining constants of the model F (GP1, GP2, . . . , GPX; D, S) by statistical data processing and modelling from
(Continued)

analyzed population. Comparing obtained result F for the investigated person with a statistically determined threshold T, which defines the threshold of increased risk for type 2 diabetes (T2D) development in the future.

8 Claims, 4 Drawing Sheets

(51) Int. Cl.
  *G01N 30/72* (2006.01)
  *G16B 5/00* (2019.01)
  *G16B 40/00* (2019.01)
  *G16B 25/00* (2019.01)
  *G01N 30/02* (2006.01)

(52) U.S. Cl.
  CPC .................. *G01N 2570/00* (2013.01); *G01N 2800/042* (2013.01); *G01N 2800/50* (2013.01); *G16B 5/00* (2019.02); *G16B 25/00* (2019.02); *G16B 40/00* (2019.02)

(58) Field of Classification Search
  CPC ..... G01N 2800/7028; G01N 33/57488; G01N 33/5091; G01N 33/6803; G01N 33/6842; G16B 40/10
  USPC .................................. 250/281, 282; 702/19
  See application file for complete search history.

(56) References Cited

OTHER PUBLICATIONS

Gornik et al., Changes of serum glycans during sepsis and acute pancreatitis, Glycobiology, vol. 17, No. 12, Oct. 15, 2007, pp. 1321-1332.
Gornik et al., Glycosylation of serum proteins in inflammatory diseases, Disease Markers 25 (2008) pp. 267-278.
Gornik et al., Change in transferrin sialylation is a potential prognostic marker for severity of acute pancreatitis, Chemical Biochemistry 41 (2008) pp. 504-510.
Itoh et al., Analysis of N-glycan in serum glycoproteins from db/db mice and humans with type 2 diabetes, Am J Physiol Endoncrinol Metab 293: 2007, pp. E1069-E1077.
Lovrencic et al. Hemoglobin A1c and the Quality of Diabetes Care, Lijec. Vjesn. 137 (2015), pp. 292-296 (Englilsh Abstract).
Opdenakker et al., Concepts and principles of glycobiology, The FASEB Journal, vol. 7, Nov. 1993, pp. 1330-1337.
Saldova et al., Association of N-Glycosylation with Breast Carcinoma and Systemic Features Using High-Resolution Quantitative UPLC, Journal of Proteome Research, 2014, 13, pp. 2314-2327.
Testa et al., N-Glycomic Changes in Serum Proteins in Type 2 Diabetes Mellitus Correlate with Complications and with Metabolic Syndrome Parameters, PLOS ONE, Mar. 20, 2015, 16 pages.
International Search Report issued in PCT/EP2017/063619 dated Jul. 20, 2017, 5 pages.
Written Opinion of the International Searching Authority issued in PCT/EP2017/063619 dated Jul. 20, 2017, 11 pages.

* cited by examiner

PROCEDURE OF PREDICTING TYPE 2 DIABETES DEVELOPMENT THROUGH ANALYSIS OF N-GLYCANS ATTACHED TO THE PLASMA PROTEINS OF A HEALTHY PERSON

CROSS REFERENCE TO RELATED APPLICATIONS

This application is the U.S. National Phase Application of PCT/EP2017/063619, filed Jun. 5, 2017, which claims priority to Croatian Patent Application No. P20160662A, filed Jun. 13, 2016, the contents of such applications being incorporated by reference herein.

DESCRIPTION

Field of the Invention

The present invention relates to a procedure of predicting type 2 diabetes (T2D) development through quantitative analysis of N-glycans attached to the plasma proteins of a healthy person.

Technical Problem

The present invention solves a technical problem of determining the risk for type 2 diabetes (T2D) development in the future for currently healthy person.

The present invention solves the above cited technical problem by using quantitative analysis of N-glycans attached to the plasma proteins of the investigated person through single analysis.

Previous State of the Art

Glycans are complex carbohydrates, which are often attached to the proteins and involved in numerous physiological and pathological processes. Therefore, their diagnostic potential as biomarkers of various physiological and pathological states is well known; see reference 1, which is incorporated by reference herein:
(1) G. Opdenakker, P. M. Rudd, C. P. Ponting, R. A. Dwek: Concepts and principles of glycobiology, *FASEB J.* 7 (1993) 1330-1337.

In this way, quantitative analysis of N-glycans attached to the plasma proteins can serve for various diagnostic purposes. Consequently, N-glycan analysis can enable drawing of conclusions on the pathological conditions of the investigated person, such as: sepsis, acute pancreatitis, inflammation and other diseases and conditions; see references 2-4, which are incorporated by reference herein:
(2) O. Gornik, L. Royle, D. J. Harvey, C. M. Radcliffe, R. Saldova, R. A. Dwek, P. Rudd, G. Lauc: Changes of serum glycans during sepsis and acute pancreatitis, *Glycobiology* 17 (2007) 1321-1332;
(3) O. Gornik, I. Gornik, V. Gašparović, G. Lauc: Change in transferrin sialylation is a potential prognostic marker for severity of acute pancreatitis, *Clin. Biochem.* 41 (2008) 504-510;
(4) O. Gornik, G. Lauc: Glycosylation of serum proteins in inflammatory diseases, *Dis. Markers* 25 (2008) 267-278.

Diabetes stands out as one of the most significant disease of the modern age, particularly due to its frequency. Type 2 diabetes (T2D) also represents one of the most significant global epidemiological problems. It is estimated that by the year 2025 the prevalence of diabetes will increase to 7.3%.

Itoh et al have investigated murine and human plasma N-glycan changes in type 2 diabetes (T2D), where they noted increased levels of biantennary glycans with α-1,6-fucose and bisecting N-acetylglucosamine, in both species. Increased level and activity of liver α-1,6-fucosyltransferase was assumed. The authors concluded that the increased level of α-1,6-fucosylation is indicative for T2D pathophysiology. Additionally, their results suggest the possibility of utilizing the N-glycan analysis and, specifically, a-1,6-fucosylation levels, for the purpose of T2D diagnosis; see reference 5, which is incorporated by reference herein:
(5) N. Itoh, S. Sakaue, H. Nakagawa, M. Kurogochi, H. Ohira, K. Deguchi, S.-I. Nishimura, M. Nishimura: Analysis of N-glycan in serum glycoproteins from db/db mice and humans with type 2 diabetes, *Am. J. Physiol. Endocrinol. Metab.* 293 (2007) E1069-E1077.

Testa et al have described significant changes of plasma N-glycan profile in patients with type 2 diabetes (T2D) and metabolic syndrome (MS), compared to healthy controls. They observed significant decrease in monogalactosylated N-glycans with α-(1,6)- and α-(1,3)-galactosylation, and core fucosylated biantennary N-glycans NG1(6)A2F and NG1(3)A2F in patients with T2D; see reference 6, which is incorporated by reference herein:
(6) R. Testa, V. Vanhooren, A. R. Bonfigli, M. Boemi, F. Olivieri, A. Ceriello, S. Genovese, L. Spazzafumo, V. Borelli, M. G. Bacalini, S. Salvioli, P. Garagnani, S. Dewaele, C. Libert, C. Franceschi: N-Glycomic Changes in Serum Proteins in Type 2 Diabetes Mellitus Correlate with Complications and with Metabolic Syndrome Parameters, *PLOS One* (2015) DOI: 10.1371/journal.pone.0119983.

It is explicitly stated that the serum N-glycans can be used as non-invasive biomarkers of type 2 diabetes; see the conclusion of the paper.

Facts indicated in the references (5) and (6) denote the possibility of diagnostics of already developed diabetes through analysis of plasma N-glycans. However, findings described in references (5) and (6) do not point out the direct possibility of using plasma N-glycans for the purpose of predicting the possibility for diabetes development in the future, for currently healthy person.

The very concept of predicting diabetes development in the future, for currently healthy person, is known in the state of the art. For example, Urdea et al have devised a diagnostic procedure for diabetes prediction 1, 2.5, 5, 7.5 or 10 years before potential onset of the disease, by analyzing specific combination of biochemical markers derived from the plasma of investigated person, which are:
1. blood glucose;
2. triglycerides; and
3. adiponectin (protein);
along with a mathematical model which predicts probability of diabetes development in investigated person; see reference (7), which is incorporated by reference herein:
(7) US 2015/193587 A1; M. S. Urdea, M. P. McKenna, P. A. Arensdorf: Diabetes-related biomarkers and methods of use thereof; Health Diagnostics Laboratory, Inc. (US).

This document indicates the possibility of diagnostic procedure wherein aforementioned key biomarkers are analyzed for investigated person, and, based on their resulting concentrations compared to the range of their concentrations in a particular population, creates prediction, i.e. probability of diabetes development in the future.

According to our best knowledge, the use of plasma N-glycans as markers for prediction of diabetes development in the future, for currently healthy person, is not described in the state of the art nor suggested in any way.

The present invention solves a technical problem of predicting or determining the risk of diabetes development in the future, for currently healthy person, as disclosed in the detailed description of the invention.

SUMMARY OF THE INVENTION

An aspect of the present invention is a procedure of determining the risk of type 2 diabetes (T2D) development in the future, for currently healthy person, based on a single quantitative analysis of plasma N-glycans, and then by employing specific mathematical models based on population study and monitoring the rate of their diabetes incidence, in a time-dependent manner.

BRIEF DESCRIPTION OF FIGURES

Logarithm of odds ratio (OR) is obtained by logistic regression and corresponds to the change of one standard deviation for each measured glycan (GP1-GP46). In order to adjust log(OR) to the change of one standard deviation (standardized log(OR)), glycan measurements were also standardized (to N (0,1) distribution) before performing logistic regression. Bar height represents the logarithm of estimated odds ratio and error bars represent 95% confidence intervals of estimated effects. y axis represents log (OR) obtained by logistic regression corresponding to the change of one standard deviation of the measured glycan.

Plasma N-glycans are analyzed by HILIC-UPLC method, according to the present invention, for patients with hyperglycemia during hospitalization in intensive care unit due to the acute illness (59 cases and 59 controls). Significant differences between cases and controls were noticed for multiple directly measured glycans. Differences in plasma glycans are shown as bars, where bar height represents effect size; the estimation is based on logistic regression and error rate, with 95% confidence interval.

Pronounced differences were observed between cases and controls. Differences in plasma glycans are shown as bar plots where height of bars represent size of effects estimated based on logistic regression (logarithm of odds ratio) and error bars represent 95% confidence intervals of estimated effects.

DETAILED DESCRIPTION OF THE INVENTION

An aspect of the present invention solves a technical problem of determining the risk for type 2 diabetes (T2D) development in the future, for currently healthy person.

A procedure according to an aspect of the invention basically comprises:
  (i) quantitative analysis of N-glycans from plasma of investigated person;
  (ii) incorporation of obtained results of N-glycan quantitative percentages into specific mathematical formulas, which were obtained in a population study and by monitoring of the rate of diabetes incidence in that population, in a time-dependent manner; and
  (iii) drawing a conclusion, based on obtained numerical result, whether the investigated person has or has not increased risk for type 2 diabetes (T2D) development in the future.

The key findings underlying an aspect of the present invention have arisen following the study on composition of plasma N-glycans of a greater population of healthy subjects (N=108) was performed.

Monitoring of Plasma N-glycan Changes and Incidence of Type 2 Diabetes (T2D) in a Larger Population Study Study recruited patients from a medical intensive care unit (ICU) in the University hospital Zagreb during period of 6 months (February to July 2013). Adult (>18 years old) patients with negative history of diabetes were eligible for participation in the study. Excluded were patients diagnosed with diabetes or prediabetes, before or during hospitalization, patients with documented gestational diabetes, pregnant patients and patients taking glucocorticoids during or 3 months before the admission.

Recruited patients were asked to attend a follow-up, 6-8 weeks after hospital discharge. At this visit inclusion/exclusion criteria were confirmed. Complete blood count and CRP were determined to exclude persisting inflammatory process. Patients with elevated markers of inflammation were retested after 2 weeks.

All patients underwent oral glucose tolerance test (OGTT) and measurement of HbA1c to identify pre-existing diabetes. ADA criteria for diagnosis of diabetes were employed and patients diagnosed with existing pre-diabetes or diabetes were excluded. Height, weight and BMI were recorded; family history of diabetes was documented.

Study included 108 patients in total, whose general characteristics are presented in Table 1.

TABLE 1

General characteristics of patients included in the study of plasma N-glycan analysis.[a]

| No. | Parameter | All patients (N = 108) | Hyper glycemia (N = 59) | No hyper glycemia (N = 49) | P-val. (HG vs. noHG) |
|---|---|---|---|---|---|
| 1 | Age (years) | 54 ± 15 | 55 ± 16 | 52 ± 14 | 0.388 |
| 2 | Female sex (N, %) | 32 (29.6) | 18 (30.5) | 14 (28.6) | 0.826 |

TABLE 1-continued

General characteristics of patients included in the study of plasma N-glycan analysis.[a]

| No. | Parameter | All patients (N = 108) | Hyper glycemia (N = 59) | No hyper glycemia (N = 49) | P-val. (HG vs. noHG) |
|---|---|---|---|---|---|
| 3 | BMI (kg/m2) | 23.7 ± 4.0 | 24.2 ± 4.1 | 23.1 ± 3.9 | 0.734 |
| 4 | Total cholesterol (mmol/L) | 4.6 ± 0.9 | 4.6 ± 0.9 | 4.6 ± 1.0 | 0.737 |
| 5 | Triglycerides (mmol/L) | 3.2 ± 1.1 | 3.2 ± 1.1 | 3.2 ± 1.1 | 0.977 |
| 6 | Family history of diabetes (N, %) | 27 (25) | 19 (32.2) | 8 (16.3) | 0.039 |

[a]Detailed study protocol is described in Example 1.

For each blood plasma sample, a quantitative analysis of N-glycans was conducted, according to the following procedure:

Quantitative Analysis of Plasma N-Glycans

Quantitative analysis of N-glycans attached to the plasma proteins comprises the following steps:
(i) collection of a blood sample from a healthy person;
(ii) isolation of plasma from the blood sample;
(iii) release of the total plasma N-glycans by enzymatic hydrolysis using N-glycosidase;
(iv) optionally, derivatization of the N-glycan mixture, using a reagent suitable to increase the detection sensitivity of such labeled N-glycans;
(v) purification of the N-glycan mixture or labeled N-glycan mixture; and
(vi) separation and quantification of N-glycans or labeled N-glycans using a suitable quantitative analytical technique.

As the suitable quantitative analytical technique for separation of plasma N-glycans any analytical technique which enables their separation and quantification can be used.

Examples of the suitable quantitative analytical technique for separation of plasma N-glycans are following techniques: ultra-performance liquid chromatography (UPLC), capillary electrophoresis (CE), MALDI-TOF mass spectrometry, liquid chromatography coupled with mass spectrometry (LC-MS) and other suitable quantitative techniques—as is well known in the state of the art; see, for example, international patent application WO2014/203010A1, where the inventors are Lauc G. et al., which is incorporated by reference.

In the present study, ultra-performance liquid chromatography (UPLC) was used, which isn't the preferred technique, just one of the many possible alternative techniques.

In an aspect of the present invention, the term N-glycan and/or N-glycan group refers to the one or more glycans originating from blood plasma, which were previously attached to the nitrogen (N—) atom within the plasma glycoprotein. During the analysis procedure, glycans are released from protein moiety using N-glycosydase F, and released carbohydrate i.e. glycan molecules are, during quantitative analysis, separated into a series of chromatographic peaks or analogue analytical signals, depending on the type of the employed analytical method. A single chromatographic peak can contain only one N-glycan or more glycans, in which case the term N-glycan group is used. More precisely, the prefix "N—" in front of the term "glycan" refers to the origin of the corresponding glycan and/or glycan group, prior to their release from the protein moiety of the glycoprotein, i.e., this means that carbohydrates (glycans) are chemically bonded to the nitrogen (N—) atoms of plasma proteins called glycoproteins.

Specifically, quantitative analysis of plasma N-glycans comprises the following steps:
(i) collection of a blood sample from a healthy person;
(ii) isolation of plasma from the blood sample;
(iii) release of the total plasma N-glycans by enzymatic hydrolysis using N-glycosidase F;
(iv) derivatization of the N-glycan mixture, using 2-aminobenzamide (2-AB) in the reaction of reductive amination, with 2-picolin-borane as reducing agent, for the purpose of N-glycan fluorescent labeling;
(v) purification of the fluorescently labeled N-glycan mixture; and
(vi) UPLC analysis of purified, fluorescently labeled N-glycans, in order to obtain quantitative percentages for each of 46 N-glycans or N-glycan groups GP1-GP46; see Table 2 and 3.

Specifically, as one of the suitable quantitative analytical methods for quantification of N-glycans showed to be ultra-performance liquid chromatography (UPLC), which is known from the literature; see reference 8, which is incorporated by reference herein:
(8) R. Saldova, A. A. Shehni, V. D. Haakensen, I. Steinfeld, M. Hilliard, I. Kifer, Å. Helland, Z. Yakhini, A.-L. Børresen-Dale, P. M. Rudd: Association of N-Glycosylation with Breast Carcinoma and Systemic Features Using High-Resolution Quantitative UPLC, J. Proteome Res. 13 (2014) 2314-2327.

Aforementioned UPLC analytical method has been performed using following conditions:
(i) column: Waters BEH;
(ii) mobile phase: mixture of solvent A=100 mM aqueous solution of ammonium formate, pH=4,4; B=acetonitrile; linear gradient of 70-53%, V/V, acetonitrile;
(iii) flow rate: 0.56 ml/min;
(iv) temperature: 25° C.;
(v) detection: fluorescence detector set at excitation wave length of 250 nm and emission wave length of 428 nm; and
(vi) analytical run: 25 min.

Figure 1:
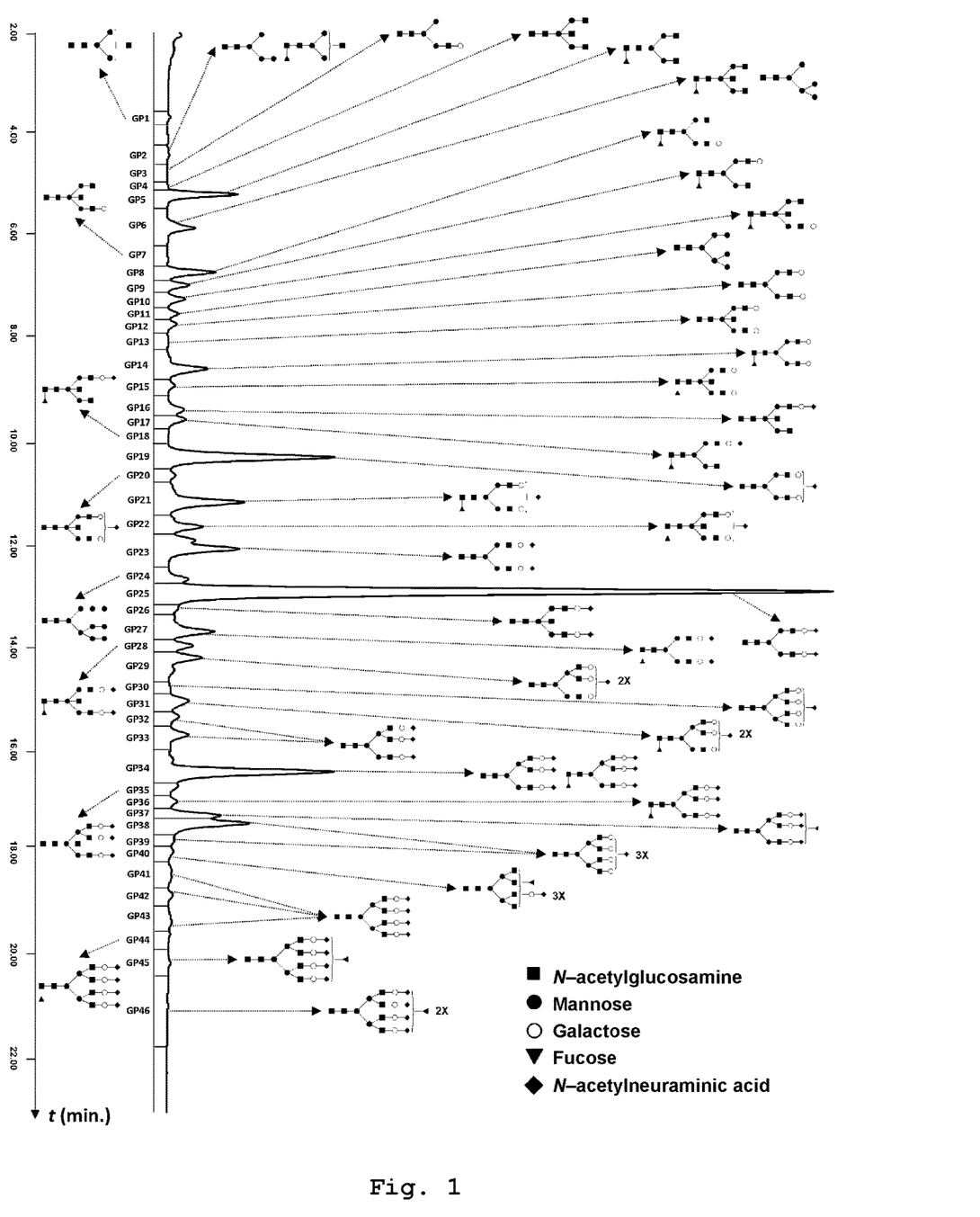
FIG. 1—depicts typical chromatogram obtained by quantitative analysis of plasma N-glycans, fluorescently labeled with 2-aminobezamide (2-AB), when employing ultra-performance liquid chromatography based on hydrophilic interactions (HILIC-UPLC), according to the method of analysis of the present invention, see Example 2.

Using the described UPLC method, a good separation of all 46 fluorescently (2AB) labeled glycans or glycan groups (GP1-GP46) is achieved, where the typical chromatogram is shown FIG. 1.

Details of the implementation of this analytical method are described in Example 2, while retention times of N-glycan groups, previously fluorescently labeled with 2-aminobenzamide, as shown in Table 2.

TABLE 2

Retention times ($t_R$) of 46 fluorescently labeled plasma N-glycans or N-glycan groups (GP1-GP46) obtained in ultra-performance liquid chromatography (UPLC) analysis.[a]

| GP | $t_R$ [min] |
|---|---|
| 1 | 3.9 |
| 2 | 4.8 |
| 3 | 5.1 |
| 4 | 5.4 |
| 5 | 5.6 |
| 6 | 6.2 |
| 7 | 6.8 |

TABLE 2-continued

Retention times ($t_R$) of 46 fluorescently labeled plasma N-glycans or N-glycan groups (GP1-GP46) obtained in ultra-performance liquid chromatography (UPLC) analysis.[a]

| GP | $t_R$ [min] |
|---|---|
| 8 | 7.2 |
| 9 | 7.4 |
| 10 | 7.6 |
| 11 | 7.9 |
| 12 | 8.2 |
| 13 | 8.5 |
| 14 | 9.1 |
| 15 | 9.3 |
| 16 | 9.9 |
| 17 | 10.0 |
| 18 | 10.4 |
| 19 | 10.8 |
| 20 | 11.2 |
| 21 | 11.7 |
| 22 | 12.1 |
| 23 | 12.5 |
| 24 | 12.9 |
| 25 | 13.3 |
| 26 | 13.6 |
| 27 | 14.1 |
| 28 | 14.3 |
| 29 | 14.7 |
| 30 | 15.1 |
| 31 | 15.4 |
| 32 | 15.9 |
| 33 | 16.1 |
| 34 | 16.8 |
| 35 | 17.1 |
| 36 | 17.4 |
| 37 | 17.6 |
| 38 | 17.8 |
| 39 | 18.1 |
| 40 | 18.4 |
| 41 | 18.7 |
| 42 | 19.1 |
| 43 | 19.6 |
| 44 | 19.9 |
| 45 | 20.4 |
| 46 | 20.7 |

[a] N-glycans are labeled with 2-aminobenzamide (1) in the reaction of reductive amination, with 2-picolin-borane as reducing agent (2PB). UPLC method: column: Waters BEH; mobile phase: mixture of solvent A = 100 mM aqueous solution of ammonium formate, pH = 4,4; B = acetonitrile; linear gradient of 70-53%, V/V, acetonitrile; flow rate: 0.56 ml/min; temperature: 25° C.; detection: fluorescence detector set at excitation wave length of 250 nm and emission wave length of 428 nm; analytical run: 25 min.

However, each chromatographic peak in the chromatogram shown in FIG. 1 contains one or more structurally similar glycans (GP1-GP46), which chemical structures are shown in Table 3.

TABLE 3

Chemical structures of N-glycans or N-glycan groups separated as individual chromatographic peaks (GP1-GP46) in the chromatogram shown in FIG. 1, according to the analytical method described in Example 2; see reference 8.

| GP | Structure |
|---|---|
| GP1 | A1 |
| GP2 | M4 |
|  | FA1 |
|  | A2 |
| GP3 | A1[6]G1 |
| GP4 | A2B |
|  | A1[3]G1 |
| GP5 | FA2 |
| GP6 | M5 |
|  | FA2B |
|  | FA1[6]G1 |
|  | A2[6]G1 |
|  | FA1[3]G1 |
|  | A2[3]G1 |
| GP7 | A2[6]BG1 |
| GP8 | A2[3]BG1 |
|  | FA2[6]G1 |
|  | M4A1G1 |
| GP9 | FA2[3]G1 |
| GP10 | FA2[6]BG1 |
| GP11 | FA2[3]BG1 |
|  | M6D1 or D2 |
|  | M6D3 |
| GP12 | A1[3]G1S[3]1 |
|  | A2G2 |
| GP13 | A1[3]G1S[6]1 |
|  | A2BG2 |
| GP14 | M5A1G1 |
|  | FA2G2 |
|  | A2[3]G1S[3]1 |
|  | A2[3]G1S[6]1 |
|  | FA1G1S[3]1 |
|  | FA1G1S[6]1 |
| GP15 | FA2BG2 |
|  | M7D3 |
|  | A2[6]BG1S[3]1 |
|  | A2[6]BG1S[6]1 |
| GP16 | A2[3]BG1S[3]1 |
|  | A2[3]BG1S[6]1 |
|  | FA2[6]G1S[3]1 |
|  | FA2[6]G1S[6]1 |
|  | M4A1G1S[3]1 |
|  | M4A1G1S[6]1 |
|  | M7D1 |
| GP17 | FA2[3]G1S[3]1 |
|  | FA2[3]G1S[6]1 |
|  | FA2[6]BG1S[3]1 |
|  | FA2[6]BG1S[6]1 |
| GP18 | FA2[3]BG1S[3]1 |
|  | FA2[3]BG1S[6]1 |
| GP19 | A2G2S[3]1 |
|  | A2G2S[6]1 |
|  | A3G3 |
| GP20 | A2BG2S[3]1 |
|  | A2BG2S[6]1 |
|  | M5A1G1S[3]1 |
|  | M5A1G1S[6]1 |
|  | FA3G3 |
|  | M8D2,D3 |
|  | A2G2S[3]1 |
| GP21 | FA2G2S[3]1 |
|  | FA2G2S[6]1 |
|  | M8D1,D3 |
| GP22 | FA2BG2S[3]1 |
|  | FA2BG2S[6]1 |
| GP23 | A2F1G2S[3]1 |
|  | A2F1G2S[6]1 |
|  | A2G2S[3,3]2 |
|  | A2G2S[3,6]2 |
|  | FA2G2S[3,3]2 |
| GP24 | A3G3S[3]1 |
|  | A3G3S[6]1 |
|  | M9 |
| GP25 | A3BG3S[3]1 |
|  | A3BG3S[6]1 |
|  | A2G2S[3,3]2 |
|  | A2G2S[3,6]2 |
|  | A2G2S[6,6]2 |
| GP26 | FA3G3S[3]1 |
|  | FA3G3S[6]1 |
|  | FA3BG3S[3]1 |

TABLE 3-continued

Chemical structures of N-glycans or N-glycan groups separated as individual chromatographic peaks (GP1-GP46) in the chromatogram shown in FIG. 1, according to the analytical method described in Example 2; see reference 8.

| GP | Structure |
|---|---|
|  | A2BG2S[3,3]2 |
|  | A2BG2S[3,6]2 |
|  | A2BG2S[6,6]2 |
| GP27 | A3F1G3S[3]1 |
|  | FA2G2S[3,3]2 |
|  | FA2G2S[3,6]2 |
|  | FA2G2S[6,6]2 |
| GP28 | FA2BG2S[3,3]2 |
|  | FA2BG2S[3,6]2 |
|  | FA2BG2S[6,6]2 |
|  | A2F1G2S[3,3]2 |
|  | A2F1G2S[3,6]2 |
|  | A2F1G2S[6,6]2 |
|  | M9Glc |
| GP29 | A3G3S[3,3]2 |
|  | A3G3S[3,6]2 |
|  | A3G3S[6,6]2 |
|  | A3BG3S[3,3]2 |
|  | A3BG3S[3,6]2 |
|  | A3BG3S[6,6]2 |
| GP30 | A4G4S[3]1 |
| GP31 | FA3G3S[3,3]2 |
|  | FA3G3S[3,6]2 |
|  | FA3G3S[6,6]2 |
|  | A3G3S[3,3]2 |
| GP32 | A3G3S[3,3,3]3 |
|  | A3F1G3S[3,3]2 |
|  | A4G4S[6]1 |
| GP33 | A3G3S[3,3,6]3 |
|  | A3G3S[3,6,6]3 |
|  | A3BG3S[3,3,3]3 |
|  | A3BG3S[3,3,6]3 |
|  | A3BG3S[3,6,6]3 |
| GP34 | FA3G3S[3,3,3]3 |
|  | FA3BG3S[3,3,3]3 |
|  | A4G4S[3,6]2 |
|  | A3G3S[3,3,3]3 |
|  | A3G3S[3,3,6]3 |
|  | A3G3S[3,6,6]3 |
|  | A3G3S[6,6,6]3 |
| GP35 | A3BG3S[3,3,3]3 |
|  | A3BG3S[3,3,6]3 |
|  | A3BG3S[6,6,6]3 |
| GP36 | FA3G3S[3,3,3]3 |
|  | FA3G3S[3,3,6]3 |
|  | FA3G3S[3,6,6]3 |
|  | FA3G3S[6,6,6]3 |
| GP37 | A3G3S[3,3,3]3 |
|  | A3G3S[3,3,6]3 |
|  | A3G3S[3,6,6]3 |
|  | A3F1G3S[3,3,3]3 |
|  | A3F1G3S[3,3,6]3 |
|  | FA3BG3S[3,3,3]3 |
|  | FA3BG3S[6,6,6]3 |
| GP38 | A4G4S[3,3,3]3 |
|  | A3F1G3S[3,6,6]3 |
| GP39 | A4G4S[3,3,6]3 |
|  | A4G4S[3,6,6]3 |
| GP40 | A4F1G3S[3,3,3]3 |
|  | A3F2G3S[3,3,3]3 |
|  | A4F1G3S[3,3,6]3 |
|  | A4F1G3S[3,6,6]3 |
| GP41 | A3F2G3S[3,3,6]3 |
|  | A4F2G3S[3,3,3]3 |
|  | A4F2G3S[3,3,6]3 |
|  | *A4G4S[3,3,3,3]4 |
|  | A4G4S[3,3,3,6]4 |
| GP42 | A4G4S[3,3,3,6]4 |
| GP43 | *A4G4S[3,3,3,6]4 |
|  | A4G4S[3,3,6,6]4 |
|  | A4G4S[3,6,6,6]4 |
| GP44 | *A4G4S[3,3,3,3]4 |
|  | FA4G4S[3,3,3,3]4 |
|  | FA4G4S[3,3,3,6]4 |
|  | A4BG4S[3,3,6,6]4 |
| GP45 | A4F1G4S[3,3,3,3]4 |
|  | A4F1G4S[3,3,3,6]4 |
|  | A4F1G4S[3,3,6,6]4 |
|  | A4F1G4S[3,6,6,6]4 |
| GP46 | A4G4LacS[3,3,3,3]4 |
|  | A4G4LacS[3,3,3,6]4 |
|  | A4F2G4S[3,3,3,3]4 |
|  | A4F2G4S[3,3,6,6]4 |
|  | A4F3G4S[3,3,3,3]4 |

GP = glycan group;
*Glycans with identical composition, but isomeric structures, with differently linked sialic acid.

Described quantification of N-glycans was performed for all blood plasma samples from the described study on examining of glycome composition in aforementioned population of patients.

The obtained results of the quantitative composition of N-glycans are compared between two groups of patients:
(i) those with documented hyperglycemia during acute illness (known increased risk for T2D development); and
(ii) those who remained normoglycemic during acute illness;

See Table 1.

Based on statistical data processing, a model that discriminates the aforementioned two groups of patients was formed. The aforementioned model is based on the overall glycan profile, on which basis a ROC (Receiver Operating Characteristic) curve was formed; see FIG. 2.

Figure 2:
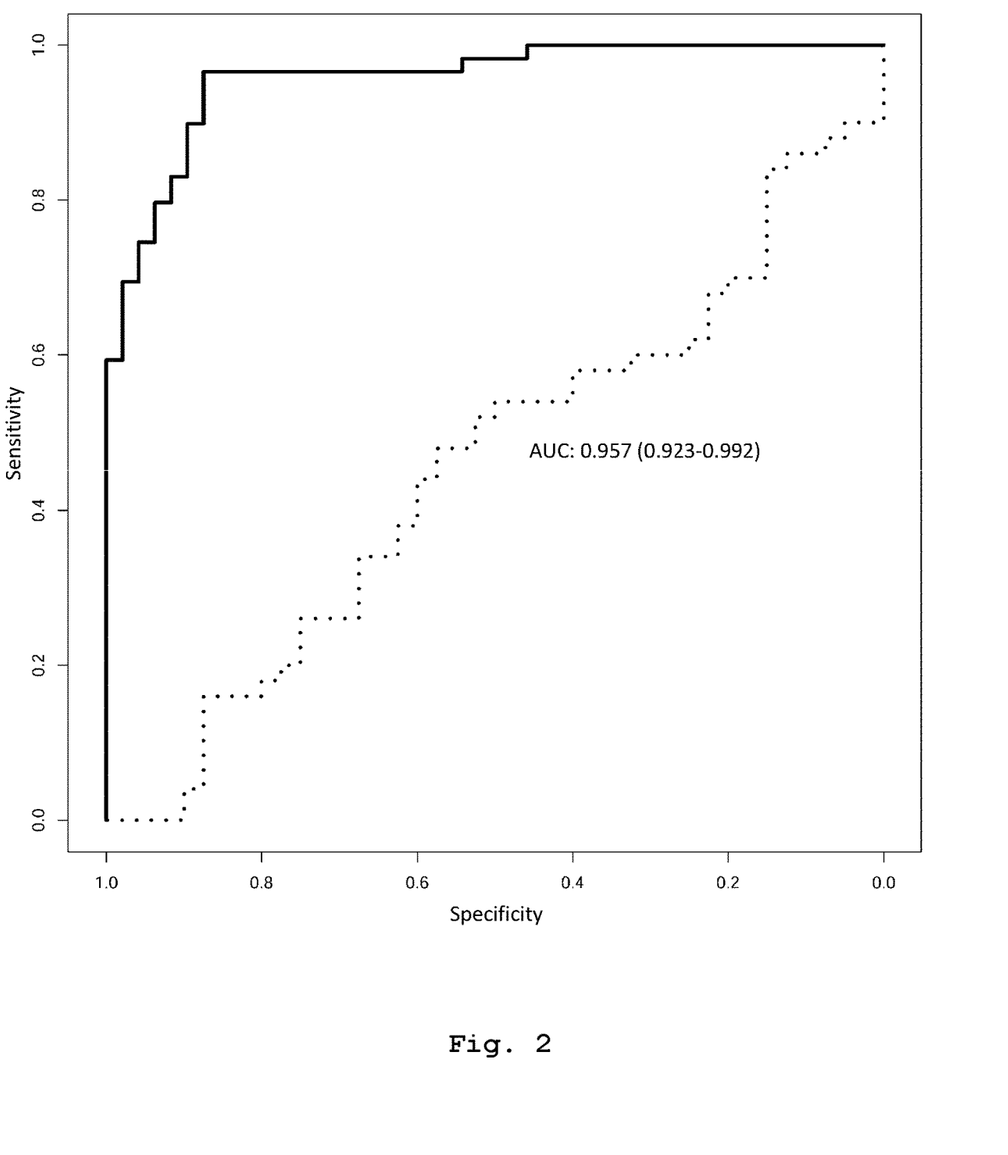
FIG. 2—depicts ROC (Receiver Operating Characteristic) curve (full line) discriminating between patients with hyperglycemia in acute disease (increased risk for type 2 diabetes development) and patients with normal blood glucose levels in acute disease. ROC curve is constructed using total plasma N-glycome as predictor. Furthermore, FIG. 2 also depicts ROC curve (dotted line) displaying discriminative value of glycated hemoglobin (HbA1c), as standard diagnostic marker for type 2 diabetes in the state of the art.

The ROC curve analysis shown in FIG. 2 describes a discriminatory model for the diagnosis of hyperglycemia in patients with acute illness (increased risk of T2D development). Regularized logistic regression was used for classification analysis, where all 46 plasma glycans were used as predictors. The ROC curve is defined on the basis of the validation set obtained by the "leave-one-out" crossover validation (10CV).

It is evident from FIG. 2, that the plasma N-glycome significantly discriminates, with high sensitivity and specificity, between patients with hyperglycemia during the acute illness and patients who remained normoglycemic during the same condition.

For comparison, FIG. 2 also shows the ROC curve for the discriminatory power of glycated hemoglobin (HbA1c), which is the standard marker for hyperglycemia diagnostics or the success of type 2 diabetes treatment, from the state of the art; see reference 9, which is incorporated by reference, herein:

(9) M. Vučić Lovrenčić, L. Smirčić Duvnjak, D. Rahelić: [Hemoglobin A1c and the Quality of Diabetes Care], *Lijec. Vjesn.* 137 (2015) 292-296.

It is evident from FIG. 2, that plasma glycans have significantly higher discriminatory power as biomarkers, compared to glycated hemoglobin (HbA1c) from the state of the art, so that HbA1c couldn't serve as a marker for T2D predisposition in our examined population.

Although hyperglycemia during acute illness identifies patients at high risk of type 2 diabetes (T2D) development, it is possible to apply it as a prediction method only to patients who have been admitted to the Intensive Care Unit (ICU) with acute illness. Glycans as indirect, but highly reliable, predictors of hyperglycemia in acute illness are much better biomarkers for the risk of T2D development, because analysis can be carried out for currently healthy person by simple analysis of a blood sample.

In the following steps of data analysis, in order to make possible conclusions about the nature of predisposition for diabetes development, glycans are divided into:
(i) high branched glycans (HB);
(ii) low branched glycans (LB);
(iii) neutral glycans (S0);
(iv) according to the degree of sialylation: monosialylated (S1), disialylated (S2), trisialylated (S3), tetrasialylated (S4); and
(v) according to the degree of galactosylation: agalactosylated (G0), monogalactosylated (G1), digalactosylated (G2), trigalactosylated (G3) and tetragalactosylated (G4) glycans.

The aforementioned glycan types are composed of the following individual glycans or glycans groups:

$HB=GP29+GP30+GP31+GP32+GP33+GP34+$
$GP35+GP36+GP37+GP38+GP39+GP40+$
$GP41+GP42+GP43+GP44+GP45+GP46$ $LB=GP1+GP2+GP3+GP4+GP5+GP6+GP7+GP8+$
$GP9+GP10+GP11+GP12+GP13+GP14+GP15+$
$GP16+GP17+GP18+GP19+GP20+GP21+$
$GP22+GP23+GP24+GP25+GP26+GP27+GP28$ $S0=GP1+GP2+GP3+GP4+GP5+GP6+GP7+GP8+$
$GP9+GP10+GP11+GP12+GP13+GP14+GP15$ $S1=GP16+GP17+GP18+GP19+GP20+GP21+GP22+GP30$ $S2=GP23+GP25+GP26+GP27+GP28+GP29+GP31$ $S3=GP32+GP33+GP34+GP35+GP36+GP37+GP38+GP39+GP40$ $S4=GP41+GP42+GP43+GP44+GP45+GP46$ $G0=GP1+GP2+GP4+GP5+GP6$ $G1=GP3+GP7+GP8+GP9+GP10+GP16+GP17+GP18$ $G2=GP12+GP13+GP14+GP15+GP19+GP20+GP21+GP22+GP23+GP25+GP26+GP27+GP28$ $G3=GP29+GP31+GP32+GP33+GP34+GP35+GP36+GP37+GP40$ $G4=GP30+GP38+GP39+GP41+GP42+GP43+GP44+GP45+GP46$

Figure 4:
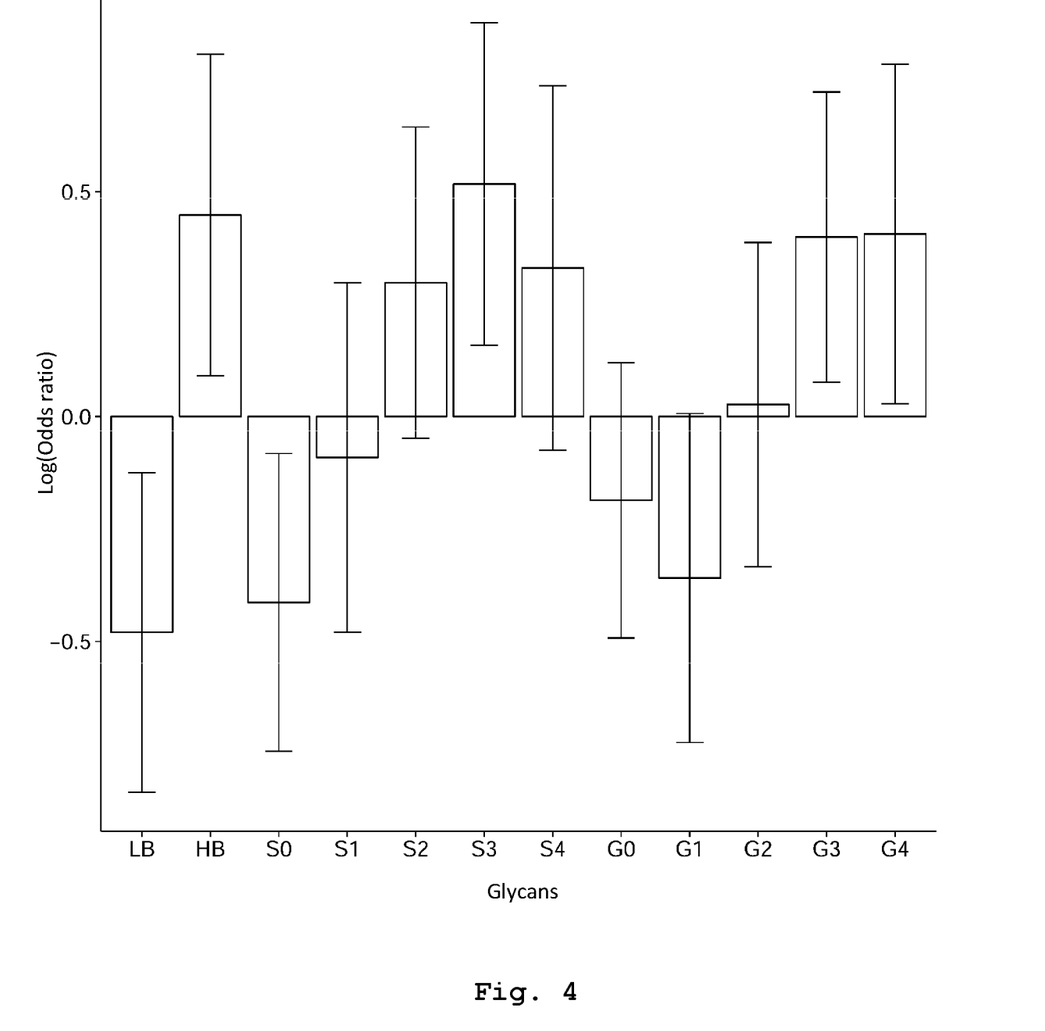
FIG. 4—depicts differences in abundances of plasma glycans, expressed as logarithm of odds ratio; as in FIG. 2, only now x-axis represents different groups of glycans with similar features: high branching (HB); low branching (LB); neutral glycans (S0); sialylated glycans: monosialylated (S1), disialylated (S2), trisialylated (S3), tetrasialylated (S4); and regarding galactosylation level: agalactosylated (G0), monogalactosylated (G1), digalactosylated (G2), trigalactosylated (G3) and tetragalactosylated (G4) glycans.

A significant difference between people with high risk for T2D development (hyperglycemic group) and controls has been noted; see FIG. 4.

FIG. 4 clearly shows the feature which appears in the population, that the predisposition for type 2 diabetes (T2D) is characterized by high branched glycans (HB). Statistically significantly different, the simple ratio of high branched (HB) to low branched (LB) glycans is a good discriminative parameter to determine whether the examined, currently healthy person has or has not increased risk for type 2 diabetes (T2D) development in the future; see FIG. 4.

Details of statistical data processing from the study are described in Example 3.

In the described manner, it is possible to conduct a diagnostic procedure of prediction of the type 2 diabetes development (T2D) in the future, for currently healthy person.

The Procedure of Predicting Type 2 Diabetes Development Through Analysis of N-Glycans Attached to the Plasma Proteins of a Healthy Person The same method, as described earlier, is used as the diagnosis protocol through quantitative analysis of N-glycans attached to the plasma proteins of a healthy person. The results of quantitative analysis of all N-glycans are included in a mathematical formula A and/or B. The obtained numerical values are used to conclude if a currently healthy person has a significant probability for type 2 diabetes development in the future.

The diagnosis procedure, according to an aspect of the invention, comprises the following steps:
(i) collection of a blood sample from a healthy person;
(ii) isolation of plasma from the blood sample;
(iii) release of the total plasma N-glycans by enzymatic hydrolysis using N-glycosidase;
(iv) optionally, derivatization of the N-glycan mixture, using a reagent suitable to increase the detection sensitivity of such labeled N-glycans;
(v) purification of the N-glycan mixture or derivatized N-glycan mixture;
(vi) separation and quantification of N-glycans or derivatized N-glycans using a suitable quantitative analytical technique;
(vii) quantitative percentages of all N-glycans, obtained as described in the step (vi), are used as input variables of the following model:

$F(GP1,GP2,\ldots,GPX;D,S)$ where X, D and S are the parameters of the model F with following meaning:
X=total number of analyzed N-glycans from GP1 to GPX;
D=age of the investigated person;
S=sex of the investigated person; male=1, female=0;
where the model constants are obtained by statistical data processing from analyzed population; and
(viii) where the result F obtained in step (vii) for investigated person is compared with a threshold T, which is statistically determined on the same population and which defines increased risk for type 2 diabetes (T2D) development in the future.

Specifically, the diagnosis procedure, according to an aspect of the invention, comprises the following steps:
(i) collection of a blood sample from a healthy person;
(ii) isolation of plasma from the blood sample;
(iii) release of the total plasma N-glycans by enzymatic hydrolysis using N-glycosidase F;
(iv) derivatization of the N-glycan mixture, using 2-aminobenzamide (2-AB) in the reaction of reductive amination, with 2-picolin-borane as reducing agent, for the purpose of N-glycan fluorescent labeling;
(v) purification of the fluorescently labeled N-glycan mixture;
(vi) separation and quantification of fluorescently labeled N-glycans using quantitative analytical technique;
(vii) the obtained quantitative percentages of all 46 N-glycans and/or N-glycan groups, obtained as described in the step (vi), are used as input variables of the following model:

$F(GP1,GP2,\ldots,GP46;D,S)$ where D and S are the optional parameters of the model F:
D=age of the investigated person;
S=sex of the investigated person; male=1, female=0;
where the model constants are obtained by statistical data processing from analyzed population; and
(viii) where the result F obtained in step (vii) for investigated person is compared with a threshold T, which is statistically determined on the same population and which defines increased risk for type 2 diabetes (T2D) development in the future.

In one embodiment of the invention, aforementioned model F(GP1, GP2, . . . , GP46; D, S) is defined as follows; D=age of the investigated person; S=sex of the investigated person; male=1, female=0:

$$F=241.22-0.08 \cdot D+4.90 \cdot S+340.97 \cdot GP1+148.85 \cdot GP2-601.13 \cdot GP3-126.73 \cdot GP4-3.63 \cdot GP5+2.88 \cdot GP6+83.43 \cdot GP7-3.25 \cdot GP8-16.05 \cdot GP9-61.37 \cdot GP10-0.97 \cdot GP11-29.26 \cdot GP12+493.12 \cdot GP13-26.78 \cdot GP14-60.56 \cdot GP15-75.38 \cdot GP16+6.70 \cdot GP17-192.66 \cdot GP18+5.29 \cdot GP19-122.71 \cdot GP20+24.31 \cdot GP21+28.30 \cdot GP22+24.25 \cdot GP23+99.98 \cdot GP24-15.34 \cdot GP25+88.79 \cdot GP26+16.41 \cdot GP27+0.30 \cdot GP28-33.34 \cdot GP29+204.62 \cdot GP30+35.04 \cdot GP31-49.97 \cdot GP32-135.63 \cdot GP33+1.28 \cdot GP34+223.98 \cdot GP35-14.25 \cdot GP36+63.65 \cdot GP37-2.92 \cdot GP38-33.94 \cdot GP39-204.07 \cdot GP40+181.01 \cdot GP41+101.38 \cdot GP42-101.40 \cdot GP43-113.31 \cdot GP44+128.24 \cdot GP45-87.65 \cdot GP46$$

and where threshold T=−3.627; and if F>T, it means that investigated person is at an increased risk of developing type 2 diabetes (T2D) in the future.

In another embodiment of the invention, aforementioned model F(GP1, GP2, . . . , GP46) is defined as following:

$$F=-3.82+16.30 \cdot (HB/LB)$$

where HB and LB are additionally defined through quantitative glycan percentages; factor HB represents the sum of branched glycans, while factor LB represents the sum of glycans with low branching;

$$HB=GP29+GP30+GP31+GP32+GP33+GP34+GP35+GP36+GP37+GP38+GP39+GP40+GP41+GP42+GP43+GP44+GP45+GP46$$

$$LB=GP1+GP2+GP3+GP4+GP5+GP6+GP7+GP8+GP9+GP10+GP11+GP12+GP13+GP14+GP15+GP16+GP17+GP18+GP19+GP20+GP21+GP22+GP23+GP24+GP25+GP26+GP27+GP28$$

and where threshold T=0.33; and if F>T, it means that investigated person is at an increased risk of developing type 2 diabetes (T2D) in the future.

The Use of the Procedure of Predicting Type 2 Diabetes Development (T2D) of a Healthy Person The diagnostic procedure, according to an aspect of the invention, is used for predicting the risk of developing type 2 diabetes (T2D) in the future through a single plasma N-glycans analysis of a currently healthy person.

The Modes of Carrying Out Aspects of the Invention

General Remarks

The study protocol for N-glycan analysis in patients has been approved by Ethics Committees of the Clinical Hospital Zagreb, Croatia. All recruited patients have signed informed consent form for participation in the study.

Abbreviations of used reagents, devices and other abbreviations:
EDTA=ethylenediaminetetraacetic acid;
SDS=sodium dodecyl sulfate (anionic detergent);
PNGase F=peptide-N4-(N-acetyl-β-glucosaminyl)-asparagine amidase;
DMSO=dimethyl sulfoxide;
2AB=2-aminobenzamide;
2PB=2-picoline borane;
PBS=phosphate-buffered saline;
GHP filter=GH polypro (GHP) membrane filters (filter media: hydrophilic polypropylene);
Igepal-CA630=octylphenoxy-poly(ethyleneoxy)ethanol (non-ionic detergent);
UPLC=ultra-performance liquid chromatography
HILIC=hydrophilic interactions liquid chromatography

EXAMPLE 1

The Study of Determining Plasma N-Glycan Compositional Changes and the Incidence of Type 2 Diabetes (T2D) Development, in a Time-Dependent Manner Study hypothesis: To analyze plasma N-glycans, of a larger population of patients who experienced hyperglycemia during an acute inflammation, then again after 6 to 8 weeks, when it was certain that they are healthy, i.e. in a phase of normoglycemia and when the earlier disease state no longer influenced their N-glycan composition. Model that distinguishes individuals at high and low risk of type 2 diabetes development was formed by statistical analysis, on the basis of differences in the composition of N-glycans between those two patient groups.

Alternatively, the study can be performed on population of the same size, by analyzing N-glycans and archiving the results. The analysis of plasma N-glycans is then repeated on the same population after several years.

Individuals who developed type 2 diabetes during those several years are clearly classified in the high-risk group. Individuals who did not develop type 2 diabetes are classified in the low risk group for type 2 diabetes development in the future. Statistical model is then formed, by aforementioned statistical method, which distinguishes individuals at high risk from individuals at low risk of developing type 2 diabetes.

The study was performed on patients from a medical intensive care unit (ICU) at a Clinical hospital Zagreb during the period of 6 months (February to July 2013). Adult (>18 years old) patients with negative history of diabetes who were admitted to the ICU and were discharged from the hospital alive were eligible for inclusion. Excluded were patients diagnosed with diabetes or prediabetes before or during hospitalization, patients with documented gestational diabetes, pregnant patients and patients taking glucocorticoids during or 3 months before the admission.

Patients were asked to attend a follow-up, 6-8 weeks after hospital discharge. At this visit inclusion/exclusion criteria were confirmed. Complete blood count and CRP were determined to exclude persisting inflammatory process. Patients with elevated markers of inflammation were retested after 2 weeks.

All patients underwent oral glucose tolerance test (OGTT) and measurement of HbA1c to identify pre-existing diabetes. ADA criteria for diagnosis of diabetes were employed and patients diagnosed with existing pre-diabetes or diabetes were excluded. Height, weight and BMI were recorded; family history of diabetes was documented.

Blood samples for glycan profiling were taken in tubes with anticoagulants, plasma has been separated immediately and stored at −20° C. until the analysis; see the Example 2.

Individuals who developed any autoimmune, malignant or other chronic disease were excluded.

During the inclusion period, there were 241 admissions to the medical ICU, of which 203 were discharged alive from the hospital. Excluded were 48 patients because of pre-existing diabetes, 15 because of glucocorticoid therapy, 2 with a history of gestational diabetes and 1 pregnant patient. Consent was denied by 16 patients and 7 patients did not show at the follow-up visit. Another 2 patients were excluded because of persisting inflammatory process and 4 because of newly diagnosed diabetes. Remaining 108 patients were sampled for glycan profiling.

The general characteristics of 108 patients included in the present study are shown in Table 1.

EXAMPLE 2

Plasma N-Glycan Analysis (1) Collection of Blood Samples and Isolation of Plasma:

Collection of blood samples was done in accordance with good clinical practice and standard venipuncture procedure, samples were taken in tubes with anticoagulants (EDTA or citrate) and immediately further processed in order to separate blood plasma.

(2) Isolation of Blood Plasma:

The blood plasma was isolated by centrifugation, separated and then stored at −20° C. until further analysis were performed.

(3) N-Glycan Release from Plasma Proteins:

10 μL of each plasma sample was denatured with the addition of 20 μL of 2% SDS (w/v) (Invitrogen, Carlsbad, Calif., USA) and by incubation at 65° C. for 10 min. Subsequently, 10 μL of 4% Igepal-CA630 (Sigma-Aldrich, St. Louis, Mo., USA) and 1.25 mU PNGase F (ProZyme, Hayward, Calif., USA) in 10 μL 5×PBS were added. Samples were incubated overnight at 37° C. for N-glycan release.

(4) Fluorescent Labeling of Released N-Glycans by Reductive Amination with 2-aminobenzamide (2-AB):

Released N-glycans were fluorescently labeled by reductive amination with 2-aminobenzamide (2-AB). The labeling mixture was freshly prepared by dissolving 2-AB (19.2 mg/mL, Sigma-Aldrich, St. Louis, Mo., USA) and 2-picoline borane (44.8 mg/mL, Sigma-Aldrich, St. Louis, Mo., USA) in DMSO (Sigma-Aldrich, St. Louis, Mo., USA) and glacial acetic acid (Merck, Darmstadt, Germany) mixture (70:30, v/v).

25 μL of labeling mixture was added to each N-glycan sample in the 96-well plate and the plate was then sealed using an adhesive seal. Mixing was achieved by shaking for 10 min, followed by two-hour incubation at 65° C. Samples (volume of 75 μL) were brought to 80% ACN (v/v) by adding 300 μL of ACN (J.T. Baker, Phillipsburg, N.J., USA).

(5) Purification of Fluorescently Labeled N-Glycan Mixture:

Free label and reducing agent were removed from the samples using HILIC-SPE. 200 μL of 0.1 g/mL suspension of microcrystalline cellulose (Merck, Darmstadt, Germany) in water was applied to each well of a 0.45 μm GHP filter plate (Pall Corporation, Ann Arbor, Mich., USA). Solvent was removed by application of vacuum using a vacuum manifold (Millipore Corporation, Billerica, Mass., USA). All wells were prewashed using 5×200 μL water, followed by equilibration using 3×200 μL acetonitrile/water (80:20, v/v). The samples were loaded to the wells. The wells were subsequently washed 7× using 200 μL acetonitrile/water (80:20, v/v). Glycans were eluted 2× with 100 μL of water and combined eluates were stored at −20° C. until UPLC analysis was performed.

(6) Quantitative Analysis (Separation) of Fluorescently Labeled N-Glycans by Hydrophilic Interaction (HILIC) Ultra-Performance Liquid Chromatography (UPLC):

Fluorescently labeled N-glycans were separated by hydrophilic interaction ultra-performance liquid chromatography (HILIC-UPLC) on Waters Acquity instrument (Milford, Mass., USA) consisting of a quaternary solvent manager, sample manager and a FLR fluorescence detector, set at excitation and emission wavelengths of 250 and 428 nm, respectively. The instrument was under the control of Empower 2 software, build 2145 (Waters, Milford, Mass., USA). Labeled N-glycans were separated on a Waters bridged ethylene hybrid (BEH) Glycan chromatography column, 150×2.1 mm and i.d., 1.7 μm BEH particles, with 100 mM ammonium formate, pH 4.4, as solvent A and acetonitrile as solvent B. The separation method used a linear gradient of 70-53% acetonitrile (v/v) at flow rate of 0.561 ml/min in a 25 min analytical run.

Samples were maintained at 5° C. before injection, and the separation temperature was 25° C. The system was calibrated using an external standard of hydrolyzed and 2-AB labeled glucose oligomers, which served for conversion of individual glycan retention time into glucose units. Data processing was performed using an automatic processing method, with a traditional integration algorithm, after which each chromatogram was manually corrected to maintain the same intervals of integration for all samples. The chromatograms were all separated in the same manner into 46 peaks (GP1-GP46) and the amount of glycans in each peak was expressed as % of total integrated area.

The aforementioned UPLC quantitative analytical method is described in the literature; see reference 8. A typical chromatogram is shown in FIG. 1.

Figure 3:
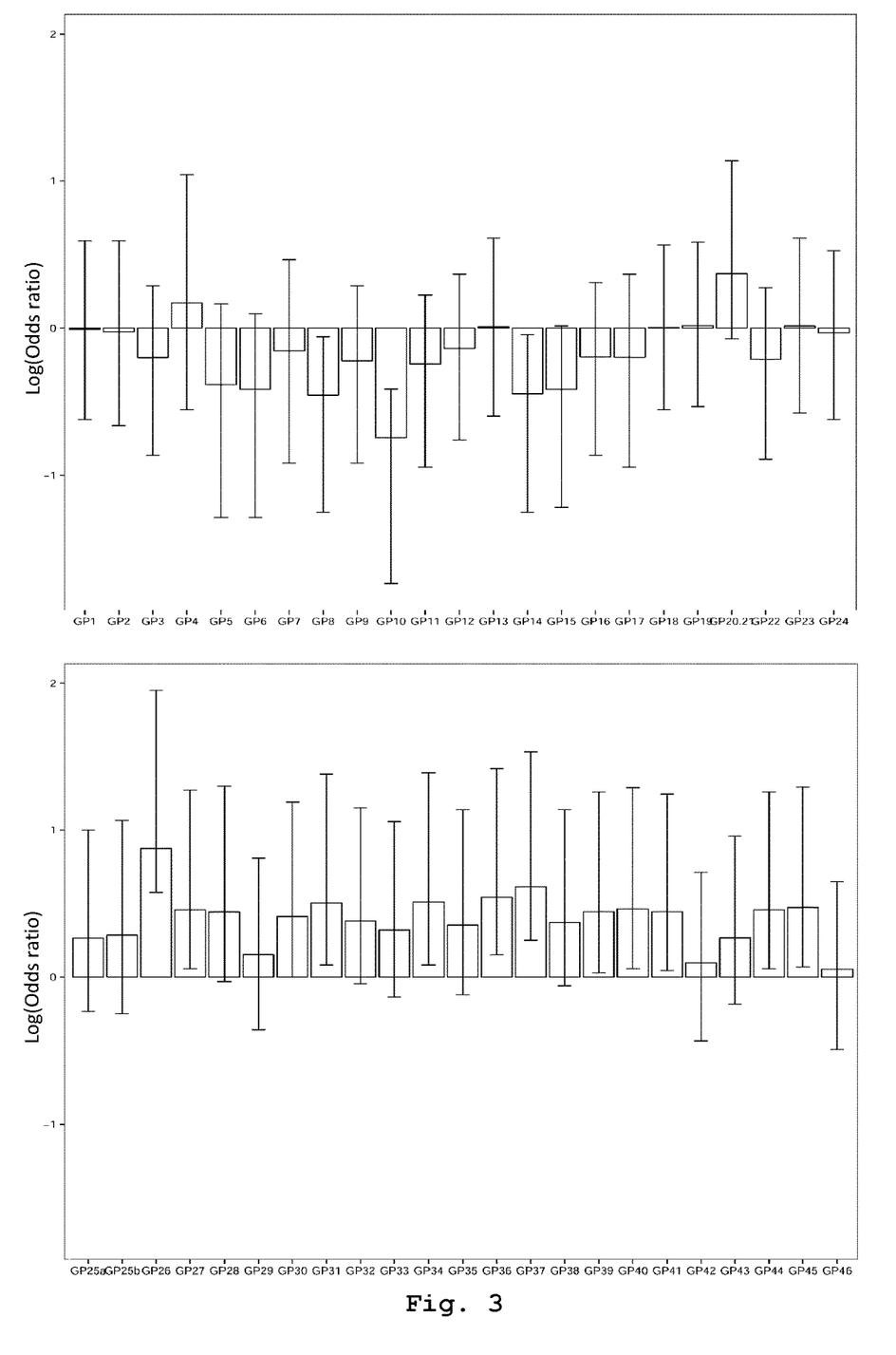
FIG. 3—depicts logarithm (logarithm base=e; here and in the entire text) of odds ratio obtained by logistic regression, which corresponds to the change of one standard deviation for each measured glycan (GP1-GP46).

(7) Incorporation of the Obtained Results of 46 N-Glycan Quantitative Percentages into Mathematical Models, According to an Aspect of the Invention, Obtained by Statistical Analysis of the Study Results, and Drawing Conclusions:

From the obtained results of quantitative analysis of 46 plasma N-glycans (GP1-GP46) of patients recruited in the study, through statistical analysis described in the Example 3 and FIGS. 2-4, two different models and two values of the threshold for determining the risk were obtained.

In one embodiment of the invention, aforementioned model $F(GP1, GP2, \ldots, GP46; D, S)$ is defined as follows; D=age of the investigated person; S=sex of the investigated person; male=1, female=0:

$$F = 241.22 - 0.08 \cdot D + 4.90 \cdot S + 340.97 \cdot GP1 + 148.85 \cdot GP2 - 601.13 \cdot GP3 - 126.73 \cdot GP4 - 3.63 \cdot GP5 + 2.88 \cdot GP6 + 83.43 \cdot GP7 - 3.25 \cdot GP8 - 16.05 \cdot GP9 - 61.37 \cdot GP10 - 0.97 \cdot GP11 - 29.26 \cdot GP12 + 493.12 \cdot GP13 - 26.78 \cdot GP14 - 60.56 \cdot GP15 - 75.38 \cdot GP16 + 6.70 \cdot GP17 - 192.66 \cdot GP18 + 5.29 \cdot GP19 - 122.71 \cdot GP20 + 24.31 \cdot GP21 + 28.30 \cdot GP22 + 24.25 \cdot GP23 + 99.98 \cdot GP24 - 15.34 \cdot GP25 + 88.79 \cdot GP26 + 16.41 \cdot GP27 + 0.30 \cdot GP28 - 33.34 \cdot GP29 + 204.62 \cdot GP30 + 35.04 \cdot GP31 - 49.97 \cdot GP32 - 135.63 \cdot GP33 + 1.28 \cdot GP34 + 223.98 \cdot GP35 - 14.25 \cdot GP36 + 63.65 \cdot GP37 - 2.92 \cdot GP38 - 33.94 \cdot GP39 - 204.07 \cdot GP40 +$$

$$181.01 \cdot GP41 + 101.38 \cdot GP42 - 101.40 \cdot GP43 - 113.31 \cdot GP44 + 128.24 \cdot GP45 - 87.65 \cdot GP46$$

and threshold T=−3.627; and if F>T, it means that investigated person is at an increased risk of developing type 2 diabetes (T2D) in the future. If F<T that risk is not pronounced.

In another embodiment of the invention, aforementioned model F(GP1, GP2, . . . , GP46) is defined in the way that does not include optional variables D and S:

$$F = -3.82 + 16.30 \cdot (HB/LB)$$

where HB and LB are additionally defined with quantitative glycan percentages; factor HB represents the sum of highly branched glycans, while factor LB represents the sum of glycans with low branching;

$$HB = GP29 + GP30 + GP31 + GP32 + GP33 + GP34 + GP35 + GP36 + GP37 + GP38 + GP39 + GP40 + GP41 + GP42 + GP43 + GP44 + GP45 + GP46$$

$$LB = GP1 + GP2 + GP3 + GP4 + GP5 + GP6 + GP7 + GP8 + GP9 + GP10 + GP11 + GP12 + GP13 + GP14 + GP15 + GP16 + GP17 + GP18 + GP19 + GP20 + GP21 + GP22 + GP23 + GP24 + GP25 + GP26 + GP27 + GP28$$

and threshold T=0.33; and if F>T, it means that investigated person is at an increased risk of developing type 2 diabetes (T2D) in the future. If F<T that risk is not pronounced.

EXAMPLE 3

Statistical Analysis

For statistical analysis, to predict hyperglycemia status, regularized logistic regression model (elastic net, lambda=0, alfa=0.1), R package "glmnet" was used; (see reference 10), which is incorporated by reference herein.

(10) Friedman et al., Regularization Paths for Generalized Linear Models via Coordinate Descent; Journal of Statistical Software found at jstatsoft.org/v33/i01.

For classification, all 46 plasma N-glycans were used as predictors. To evaluate the biomarker potential of glycans, model was trained and validated using "leave-one-out" cross-validation procedure, more specifically, a 10-cross-validation procedure (10CV). In 10CV procedure, data classification was performed in a way that one validation set contains only one sample, while the predictive model is being examined on all remaining samples. Predictions from each validation round were merged into one validation set, on which the performance of a cohort-specific model was evaluated, based on area under the curve (AUC).

Development of the Model 1:

As a model for prediction of hyperglycemia, regularized logistic regression (R package "glmnet") with parameters lambda=0 and alfa=0.1 was used.

As input variables for the classification model the following variables were used:
 (i) quantitative percentages of 46 glycans obtained by UPLC method from the Example 2;
 (ii) age of the investigated person;
 (iii) sex of the investigated person (0=female or 1=male).

The variable which is being predicted by the model is the hyperglycemia state of the investigated person (0=no hyperglycemia or 1=hyperglycemia).

Glycan measurements are not inputted into model as peak areas (raw data), but as percentages in total glycome; total area normalization is performed, where the area of each glycan peak is divided by the total area of the corresponding chromatogram; the sum of all normalized peaks is 100%.

Sex parameter is used in the model as the continuous variable; "glmnet" does not allow categorical variables to be used as the input variables.

Mentioned input variables are not transformed (log transformation) or scaled (standardization on N (0,1)).

Mentioned input variables are inputted in the "elastic net" model, and the output results are defined as y=F (GP1, GP2, . . . , GP46, S, D), where y is in the domain [−∞, +∞]. Some models can result in normalized y, for example, in interval [0,1].

The model coefficients, indicated in this aspect of the invention, are obtained by "training" of aforementioned model on 107 samples.

The model predictive power of is evaluated with the 10-cross-fold validation procedure and expressed by the ROC curve. Based on the ROC curve, the optimal threshold T=−3,627 was determined, taking into account the ratio of sensitivity and specificity of the classification model.

In the case when the model result is y>−3.627, the investigated person is classified as hyperglycemic.

Development of the Model 2:

As a model for the prediction of hyperglycemia, logistic regression was used (R package "stats").

As variables for the classification model the following variables were used:
 (i) 2 derived traits—low (LB) and high (HB) branched N-glycans;
 (ii) as a model input variable, the ratio of the two aforementioned derived traits was used.

The variable which is being predicted by the model is the hyperglycemic state of the patient (0=no hyperglycemia or 1=hyperglycemia). Mentioned variable is used in the "glm" model (family="binomial"), and the output result is defined as y=f(LB/HB)), where y is in the domain [−∞, +∞].

The model coefficients are obtained by "training" the mentioned model on 107 samples. No cross-validation procedure was applied, since the simple method was used.

Obtained ROC curves and processed results from the study on the plasma N-glycome composition from the patient population with and without hyperglycemia are shown in the FIGS. 2-4.

EXAMPLE 4

A Procedure of Predicting the Type 2 Diabetes (T2D) Development Through Quantitative Analysis of Plasma N-Glycans from Currently Healthy Person The procedure of predicting the T2D development is identical as the procedure described in the Example 2, and it comprises the following steps:

(1) Collection of Blood Samples and Isolation of Plasma:

Collection of blood samples was done in accordance with good clinical practice and standard venipuncture procedure, samples were collected in tubes with anticoagulants (EDTA or citrate) and immediately further processed in order to separate blood plasma.

(2) Isolation of Blood Plasma:

The blood plasma was isolated by centrifugation, separated and then stored at −20° C. until further analysis were performed.

(3) N-Glycan Release from Plasma Proteins:

10 µL of each plasma sample was denatured with the addition of 20 µL of 2% SDS (w/v) (Invitrogen, Carlsbad, Calif., USA) and by incubation at 65° C. for 10 min. Subsequently, 10 µL of 4% Igepal-CA630 (Sigma-Aldrich, St. Louis, Mo., USA) and 1.25 mU PNGase F (ProZyme, Hayward, Calif., USA) in 10 μL 5×PBS were added. Samples were incubated overnight at 37° C. for N-glycan release.

(4) Fluorescent Labeling of Released N-Glycans by Reductive Amination with 2-aminobenzamide (2-AB):

Released N-glycans were fluorescently labeled by reductive amination with 2-aminobenzamide (2-AB). The labeling mixture was freshly prepared by dissolving 2-AB (19.2 mg/mL, Sigma-Aldrich, St. Louis, Mo., USA) and 2-picoline borane (44.8 mg/mL, Sigma-Aldrich, St. Louis, Mo., USA) in DMSO (Sigma-Aldrich, St. Louis, Mo., USA) and glacial acetic acid (Merck, Darmstadt, Germany) mixture (70:30, v/v).

25 μL of labeling mixture was added to each N-glycan sample in the 96-well plate and the plate was then sealed using an adhesive seal. Mixing was achieved by shaking for 10 min, followed by two-hour incubation at 65° C. Samples (volume of 75 μL) were brought to 80% ACN (v/v) by adding 300 μL of ACN (J.T. Baker, Phillipsburg, N.J., USA).

(5) Purification of Fluorescently Labeled N-Glycan Mixture:

Free label and reducing agent were removed from the samples using HILIC-SPE. 200 μL of 0.1 g/mL suspension of microcrystalline cellulose (Merck, Darmstadt, Germany) in water was applied to each well of a 0.45 μm GHP filter plate (Pall Corporation, Ann Arbor, Mich., USA). Solvent was removed by application of vacuum using a vacuum manifold (Millipore Corporation, Billerica, Mass., USA). All wells were prewashed using 5×200 μL water, followed by equilibration using 3×200 μL acetonitrile/water (80:20, v/v). The samples were loaded to the wells. The wells were subsequently washed 7× using 200 μL acetonitrile/water (80:20, v/v). Glycans were eluted 2× with 100 μL of water and combined eluates were stored at −20° C. until UPLC analysis was performed.

(6) Quantitative Analysis (Separation) of Fluorescently Labeled N-Glycans by Hydrophilic Interaction (HILIC) Ultra-Performance Liquid Chromatography (UPLC):

Fluorescently labeled N-glycans were separated by hydrophilic interaction ultra-performance liquid chromatography (HILIC-UPLC) on Waters Acquity instrument (Milford, Mass., USA) consisting of a quaternary solvent manager, sample manager and a FLR fluorescence detector, set at excitation and emission wavelengths of 250 and 428 nm, respectively. The instrument was under the control of Empower 2 software, build 2145 (Waters, Milford, Mass., USA). Labeled N-glycans were separated on a Waters bridged ethylene hybrid (BEH) Glycan chromatography column, 150×2.1 mm and i.d., 1.7 μm BEH particles, with 100 mM ammonium formate, pH 4.4, as solvent A and acetonitrile as solvent B. The separation method used a linear gradient of 70-53% acetonitrile (v/v) at flow rate of 0.561 ml/min in a 25 min analytical run.

Samples were maintained at 5° C. before injection, and the separation temperature was 25° C. The system was calibrated using an external standard of hydrolyzed and 2-AB labeled glucose oligomers, which served for conversion of individual glycan retention time into glucose units. Data processing was performed using an automatic processing method, with a traditional integration algorithm, after which each chromatogram was manually corrected to maintain the same intervals of integration for all samples. The chromatograms were all separated in the same manner into 46 peaks (GP1-GP46) and the amount of glycans in each peak was expressed as % of total integrated area.

The aforementioned UPLC quantitative analytical method is described in the literature; see reference 8. A typical chromatogram is shown in FIG. 1.

(7) Incorporation of the Obtained Results of 46 N-Glycan Quantitative Percentages into Models, According to an Aspect of the Invention, the Risk Determination Methods:

After the results of 46 N-glycans quantitative percentages were obtained it was possible to use one of the offered models, previously described in the Example 2, item (7).

Discussion of the Used Models

It is interesting to notice that models are significantly different from each other according to the input parameters; a model which is based on factor HB and LB percentages has more robust application, because it is independent of sex and age of investigated person.

Created mathematical models, according to an aspect of the invention, include the fact that plasma N-glycans have a significant role in type 2 diabetes (T2D) development in currently healthy person, and can significantly contribute to the identification of individuals at an increased risk for developing T2D.

Even though some of the glycans have shown statistically significant differences between the observed groups, none of them showed to be a good individual marker for identifying the type 2 diabetes development predisposition.

On the other hand, created mathematical models, according to an aspect of the invention, which include all 46 N-glycans, show significant power of prediction of developing T2D. Highly branched (HB) N-glycans, as well as their ratio to low branched N-glycans (HB/LB), play a significant role in the model's predictive power.

Disrupted regulation of glucose levels is connected with highly branched (HB) N-glycans, because of the significant role that glucose plays in the glycosylation pathway. Partially the reason for this is the fact that glucose is the key metabolite in the hexosamine biosynthetic pathway (HBP), in which UDP-GlcNAc is formed. UDP-GlcNAc is a key monosaccharide donor, necessary for N-glycan biosynthesis initiation in the endoplasmic reticulum, and later in the Golgi apparatus where branching of N-glycans takes place.

All of the above clearly indicates the relationship between disrupted regulation of glucose and consequential increase of percentages of highly branched (HB) N-glycans. HB N-glycans, i.e. their relative ratios to the low branched (LB) N-glycans were used in the described mathematical model, according to an aspect of the invention, as a key factor in predicting the T2D development at currently healthy person.

INDUSTRIAL APPLICABILITY

Aspects of the present invention reveal the procedure for determining the risk of developing type 2 diabetes in the future at currently healthy person through quantitative analysis of plasma N-glycans. Therefore, the industrial applicability of aspects of the present invention are obvious.

The invention claimed is:
1. A procedure for predicting type 2 diabetes development through quantitative analysis of N-glycans attached to the human plasma proteins, where said quantitative analysis comprises:
(i) collection of a blood sample from a healthy person;
(ii) isolation of plasma from the blood sample;
(iii) release of the total plasma N-glycans by enzymatic hydrolysis using N-glycosidase;

(iv) optionally, derivatization of the N-glycan mixture, using a reagent suitable to increase the detection sensitivity of such labeled N-glycans;
(v) purification of the N-glycan mixture or labeled N-glycan mixture;
(vi) separation and quantification of N-glycans or labeled N-glycans using a quantitative analytical technique; and
(vii) obtained quantitative percentages of all N-glycans determined in step (vi) are used as input variables of a model:

$$F(GP1, GP2, \ldots, GPX; D, S)$$

where X, D and S are parameters of the model F with following meaning:
X=total number of analyzed N-glycans from GP1 to GPX;
D=age of the investigated person;
S=sex of the investigated person; male=1, female=0; where the model constants are obtained by statistical data processing from analyzed population; and
(viii) where the result F obtained in step (vii) for the investigated person is compared with a threshold T, which is statistically determined on the same population and which defines increased risk for type 2 diabetes (T2D) development in the future.

2. The procedure of predicting type 2 diabetes development through quantitative analysis of N-glycans attached to the human plasma proteins according to the claim 1, wherein the following N-glycans and/or N-glycan groups correspond to the structures contained in GP1, GP2, . . . GP46, as defined below:

| GP | Structure |
| --- | --- |
| GP1 | A1 |
| GP2 | M4 |
|  | FA1 |
|  | A2 |
| GP3 | A1[6]G1 |
| GP4 | A2B |
|  | A1[3]G1 |
| GP5 | FA2 |
| GP6 | M5 |
|  | FA2B |
|  | FA1[6]G1 |
|  | A2[6]G1 |
|  | FA1[3]G1 |
|  | A2[3]G1 |
| GP7 | A2[6]BG1 |
| GP8 | A2[3]BG1 |
|  | FA2[6]G1 |
|  | M4A1G1 |
| GP9 | FA2[3]G1 |
| GP10 | FA2[6]BG1 |
| GP11 | FA2[3]BG1 |
|  | M6D1 or ili D2 |
|  | M6D3 |
| GP12 | A1[3]G1S[3]1 |
|  | A2G2 |
| GP13 | A1[3]G1S[6]1 |
|  | A2BG2 |
| GP14 | M5A1G1 |
|  | FA2G2 |
|  | A2[3]G1S[3]1 |
|  | A2[3]G1S[6]1 |
|  | FA1G1S[3]1 |
|  | FA1G1S[6]1 |
| GP15 | FA2BG2 |
|  | M7D3 |
|  | A2[6]BG1S[3]1 |
|  | A2[6]BG1S[6]1 |
| GP16 | A2[3]BG1S[3]1 |
|  | A2[3]BG1S[6]1 |
|  | FA2[6]G1S[3]1 |
|  | FA2[6]G1S[6]1 |
|  | M4A1G1S[3]1 |
|  | M4A1G1S[6]1 |
|  | M7D1 |
| GP17 | FA2[3]G1S[3]1 |
|  | FA2[3]G1S[6]1 |
|  | FA2[6]BG1S[3]1 |
|  | FA2[6]BG1S[6]1 |
| GP18 | FA2[3]BG1S[3]1 |
|  | FA2[3]BG1S[6]1 |
| GP19 | A2G2S[3]1 |
|  | A2G2S[6]1 |
|  | A3G3 |
| GP20 | A2BG2S[3]1 |
|  | A2BG2S[6]1 |
|  | M5A1G1S[3]1 |
|  | M5A1G1S[6]1 |
|  | FA3G3 |
|  | M8D2,D3 |
|  | A2G2S[3]1 |
| GP21 | FA2G2S[3]1 |
|  | FA2G2S[6]1 |
|  | M8D1,D3 |
| GP22 | FA2BG2S[3]1 |
|  | FA2BG2S[6]1 |
| GP23 | A2F1G2S[3]1 |
|  | A2F1G2S[6]1 |
|  | A2G2S[3,3]2 |
|  | A2G2S[3,6]2 |
|  | FA2G2S[3,3]2 |
| GP24 | A3G3S[3]1 |
|  | A3G3S[6]1 |
|  | M9 |
| GP25 | A3BG3S[3]1 |
|  | A3BG3S[6]1 |
|  | A2G2S[3,3]2 |
|  | A2G2S[3,6]2 |
|  | A2G2S[6,6]2 |
| GP26 | FA3G3S[3]1 |
|  | FA3G3S[6]1 |
|  | FA3BG3S[3]1 |
|  | A2BG2S[3,3]2 |
|  | A2BG2S[3,6]2 |
|  | A2BG2S[6,6]2 |
| GP27 | A3F1G3S[3]1 |
|  | FA2G2S[3,3]2 |
|  | FA2G2S[3,6]2 |
|  | FA2G2S[6,6]2 |
| GP28 | FA2BG2S[3,3]2 |
|  | FA2BG2S[3,6]2 |
|  | FA2BG2S[6,6]2 |
|  | A2F1G2S[3,3]2 |
|  | A2F1G2S[3,6]2 |
|  | A2F1G2S[6,6]2 |
|  | M9Glc |
| GP29 | A3G3S[3,3]2 |
|  | A3G3S[3,6]2 |
|  | A3G3S[6,6]2 |
|  | A3BG3S[3,3]2 |
|  | A3BG3S[3,6]2 |
|  | A3BG3S[6,6]2 |
| GP30 | A4G4S[3]1 |
| GP31 | FA3G3S[3,3]2 |
|  | FA3G3S[3,6]2 |
|  | FA3G3S[6,6]2 |
|  | A3G3S[3,3]2 |
| GP32 | A3G3S[3,3,3]3 |
|  | A3F1G3S[3,3]2 |
|  | A4G4S[6]1 |
| GP33 | A3G3S[3,3,6]3 |
|  | A3G3S[3,6,6]3 |
|  | A3BG3S[3,3,3]3 |
|  | A3BG3S[3,3,6]3 |
|  | A3BG3S[3,6,6]3 |

-continued

| GP | Structure |
|---|---|
| GP34 | FA3G3S[3,3,3]3 |
|  | FA3BG3S[3,3,3]3 |
|  | A4G4S[3,6]2 |
|  | A3G3S[3,3,3]3 |
|  | A3G3S[3,3,6]3 |
|  | A3G3S[3,6,6]3 |
|  | A3G3S[6,6,6]3 |
| GP35 | A3BG3S[3,3,3]3 |
|  | A3BG3S[3,3,6]3 |
|  | A3BG3S[6,6,6]3 |
| GP36 | FA3G3S[3,3,3]3 |
|  | FA3G3S[3,3,6]3 |
|  | FA3G3S[3,6,6]3 |
|  | FA3G3S[6,6,6]3 |
| GP37 | A3G3S[3,3,3]3 |
|  | A3G3S[3,3,6]3 |
|  | A3G3S[3,6,6]3 |
|  | A3F1G3S[3,3,3]3 |
|  | A3F1G3S[3,3,6]3 |
|  | FA3BG3S[3,3,3]3 |
|  | FA3BG3S[6,6,6]3 |
| GP38 | A4G4S[3,3,3]3 |
|  | A3F1G3S[3,6,6]3 |
| GP39 | A4G4S[3,3,6]3 |
|  | A4G4S[3,6,6]3 |
| GP40 | A4F1G3S[3,3,3]3 |
|  | A3F2G3S[3,3,3]3 |
|  | A4F1G3S[3,3,6]3 |
|  | A4F1G3S[3,6,6]3 |
| GP41 | A3F2G3S[3,3,6]3 |
|  | A4F2G3S[3,3,3]3 |
|  | A4F2G3S[3,3,6]3 |
|  | *A4G4S[3,3,3]4 |
|  | A4G4S[3,3,3,6]4 |
| GP42 | A4G4S[3,3,3,6]4 |
| GP43 | *A4G4S[3,3,3,6]4 |
|  | A4G4S[3,3,6,6]4 |
|  | A4G4S[3,6,6,6]4 |
| GP44 | *A4G4S[3,3,3,3]4 |
|  | FA4G4S[3,3,3,3]4 |
|  | FA4G4S[3,3,3,6]4 |
|  | A4BG4S[3,3,6,6]4 |
| GP45 | A4F1G4S[3,3,3,3]4 |
|  | A4F1G4S[3,3,3,6]4 |
|  | A4F1G4S[3,3,6,6]4 |
|  | A4F1G4S[3,6,6,6]4 |
| GP46 | A4G4LacS[3,3,3,3]4 |
|  | A4G4LacS[3,3,3,6]4 |
|  | A4F2G4S[3,3,3,3]4 |
|  | A4F2G4S[3,3,6,6]4 |
|  | A4F3G4S[3,3,3,3]4 |
| — | — |
| — | — | where * marks isomeric glycan structures; and where specifically in the steps defined in the claim 1, the following actions are performed:

(iv) derivatization of N-glycans with 2-aminobenz-amide in the reaction of reductive amination with 2-picolin-borane as reducing agent, for the purpose of N-glycan fluorescent labeling;

(v) purification of the fluorescently labeled N-glycan mixture;

(vi) separation and quantification of fluorescently labeled N-glycans using a quantitative analytical technique; and (vii) where obtained quantitative percentage of 46 predefined N-glycans GP1-GP46, determined in step (vi), are used as input variables of a model:

$$F(GP1, GP2, \ldots, GP46; D, S)$$

where D and S are optional parameters of the model F with following meaning:

D=age of the investigated person;
S=sex of the investigated person; male=1, female=0;
and where the model constants are obtained by statistical data processing from analyzed population; and (viii) the result F obtained in step (vii) for the investigated person is compared with a threshold T, which is statistically determined on the same population and which defines increased risk for type 2 diabetes (T2D) development in the future.

3. The procedure of predicting type 2 diabetes development through quantitative analysis of N-glycans attached to the human plasma proteins according to the claim 2, wherein, the model F (GP1, GP2, . . . , GP46; D, S) is defined in the following way:

$$F = 241.22 - 0.08 \cdot D + 4.90 \cdot S + 340.97 \cdot GP1 + 148.85 \cdot GP2 - 601.13 \cdot GP3 - 126.73 \cdot GP4 - 3.63 \cdot GP5 + 2.88 \cdot GP6 + 83.43 \cdot GP7 - 3.25 \cdot GP8 - 16.05 \cdot GP9 - 61.37 \cdot GP10 - 0.97 \cdot GP11 - 29.26 \cdot GP12 + 493.12 \cdot GP13 - 26.78 \cdot GP14 - 60.56 \cdot GP15 - 75.38 \cdot GP16 + 6.70 \cdot GP17 - 192.66 \cdot GP18 + 5.29 \cdot GP19 - 122.71 \cdot GP20 + 24.31 \cdot GP21 + 28.30 \cdot GP22 + 24.25 \cdot GP23 + 99.98 \cdot GP24 - 15.34 \cdot GP25 + 88.79 \cdot GP26 + 16.41 \cdot GP27 + 0.30 \cdot GP28 - 33.34 \cdot GP29 + 204.62 \cdot GP30 + 35.04 \cdot GP31 - 49.97 \cdot GP32 - 135.63 \cdot GP33 + 1.28 \cdot GP34 + 223.98 \cdot GP35 - 14.25 \cdot GP36 + 63.65 \cdot GP37 - 2.92 \cdot GP38 - 33.94 \cdot GP39 - 204.07 \cdot GP40 + 181.01 \cdot GP41 + 101.38 \cdot GP42 - 101.40 \cdot GP43 - 113.31 \cdot GP44 + 128.24 \cdot GP45 - 87.65 \cdot GP46$$

and where threshold T=−3.627; and if F>T, it means that the investigated person is at an increased risk of developing type 2 diabetes (T2D) in the future.

4. The procedure of predicting type 2 diabetes development through quantitative analysis of N-glycans attached to the human plasma proteins according to the claim 2, wherein, the model F (GP1, GP2, GP46; D, S) is defined in the following way:

$$F = -3.82 + 16.30 \cdot (HB/LB)$$

where HB and LB are additionally defined through quantitative glycan percentages; factor HB represents the sum of branched glycans, while factor LB represents the sum of glycans with low branching;

$$HB = GP29 + GP30 + GP31 + GP32 + GP33 + GP34 + GP35 + GP36 + GP37 + GP38 + GP39 + GP40 + GP41 + GP42 + GP43 + GP44 + GP45 + GP46$$

$$LB = GP1 + GP2 + GP3 + GP4 + GP5 + GP6 + GP7 + GP8 + GP9 + GP10 + GP11 + GP12 + GP13 + GP14 + GP15 + GP16 + GP17 + GP18 + GP19 + GP20 + GP21 + GP22 + GP23 + GP24 + GP25 + GP26 + GP27 + GP28$$

and threshold T=−3.627; and if F>T, it means that the investigated person is at an increased risk of developing type 2 diabetes (T2D) in the future.

5. The procedure of predicting type 2 diabetes development through quantitative analysis of N-glycans attached to the human plasma proteins according to claim 1, wherein the suitable quantitative analytical technique is selected from the set consisting of: ultra-performance liquid chromatography (UPLC), capillary electrophoresis (CE), MALDI-TOF mass spectrometry, liquid chromatography coupled with mass spectrometry (LC-MS).

6. The procedure of predicting type 2 diabetes development through quantitative analysis of N-glycans attached to the human plasma proteins according to the claim 5, wherein the selected quantitative analytical technique is ultra-performance liquid chromatography (UPLC).

7. The procedure of predicting type 2 diabetes development through quantitative analysis of N-glycans attached to the human plasma proteins according to the claim 6, wherein ultra-performance liquid chromatography (UPLC) is performed using following conditions:
   (i) column: Waters BEH;
   (ii) mobile phase: mixture of solvent A=100 mM aqueous solution of ammonium formate, pH=4,4; B=acetonitrile; linear gradient of 70-53%, V/V, acetonitrile;
   (iii) flow: 0.56 ml/min;
   (iv) temperature: 25° C.;
   (v) detection: fluorescence detector set at excitation wave length of 250 nm and emission wave length of 428 nm; and
   (vi) analytical run: 25 min.

8. The procedure of predicting type 2 diabetes development through quantitative analysis of N-glycans attached to the human plasma proteins according to claim 1, wherein the procedure is applied on currently healthy person, with no signs of type 2 diabetes.

* * * * *